US009134257B2

(12) United States Patent
Sloat et al.

(10) Patent No.: US 9,134,257 B2
(45) Date of Patent: Sep. 15, 2015

(54) METHOD AND APPARATUS FOR IDENTIFYING DEFECTS IN SUSCEPTORS OF MICROWAVE FOOD CONTAINERS

(71) Applicant: Graphic Packaging International, Inc., Atlanta, GA (US)

(72) Inventors: Jeffrey T. Sloat, Broomfield, CO (US); Paul Abbott, Louisville, CO (US); Scott W. Middleton, Oshkosh, WI (US); Lee M. Schneider, Menasha, WI (US); Fermin P. Resurreccion, Jr., Lakewood, CO (US)

(73) Assignee: Graphic Packaging International, Inc., Atlanta, GA (US)

( * ) Notice: Subject to any disclaimer, the term of this patent is extended or adjusted under 35 U.S.C. 154(b) by 302 days.

(21) Appl. No.: 13/804,954

(22) Filed: Mar. 14, 2013

(65) Prior Publication Data

US 2014/0269815 A1     Sep. 18, 2014

(51) Int. Cl.
*G01N 22/02*     (2006.01)
*G01N 25/72*     (2006.01)

(52) U.S. Cl.
CPC ................ *G01N 22/02* (2013.01); *G01N 25/72* (2013.01)

(58) Field of Classification Search
CPC ........ G01N 22/02; G01N 25/72; A47J 36/027
USPC .................................... 73/75, 862.338; 374/5
See application file for complete search history.

(56) References Cited

U.S. PATENT DOCUMENTS

| | | | |
|---|---|---|---|
| 4,760,444 A * | 7/1988 | Nielson et al. ................ 348/129 |
| 5,209,355 A | 5/1993 | Mindermann |
| 6,013,915 A * | 1/2000 | Watkins ..................... 250/341.1 |
| 6,324,253 B1 * | 11/2001 | Yuyama et al. ................. 378/57 |
| 6,346,704 B2 * | 2/2002 | Kenway ..................... 250/341.6 |
| 6,690,016 B1 * | 2/2004 | Watkins et al. ............ 250/341.7 |
| 6,866,417 B2 * | 3/2005 | Gunawardena et al. ...... 374/141 |

(Continued)

FOREIGN PATENT DOCUMENTS

| | | |
|---|---|---|
| JP | 2012-049299 A | 3/2012 |
| WO | WO 2004-005903 A1 | 1/2004 |

OTHER PUBLICATIONS

International Search Report and Written Opinion for PCT/US2014/011019 dated Jun. 11, 2014.

*Primary Examiner* — Freddie Kirkland, III
(74) *Attorney, Agent, or Firm* — Womble Carlyle Sandridge & Rice, LLP (57) ABSTRACT

A method and apparatus are disclosed for detecting defects in susceptors of microwave food containers during production of such containers. The method comprises the steps of advancing the microwave food containers in a downstream direction along a processing path; subjecting each microwave food container as it moves along the processing path to microwave radiation sufficient to heat the susceptors of the container without destroying the susceptors of the container; obtaining an image preferably in the infrared spectrum of the heated susceptors of each container; determining if the image is indicative of a defect in the susceptors of each container; and removing from the processing path containers that are indicated to have defective susceptors. The apparatus includes a conveyor that moves containers through a first microwave absorbing cavity, a resonator cavity wherein containers are subjected to microwave energy, and a second microwave absorbing cavity wherein an image of each container is obtained.

27 Claims, 5 Drawing Sheets

(56) References Cited

U.S. PATENT DOCUMENTS

| | | | |
|---|---|---|---|
| 7,042,231 B2* | 5/2006 | Trebbi | 324/639 |
| 7,129,492 B2* | 10/2006 | Saito et al. | 250/341.6 |
| 8,097,857 B2* | 1/2012 | Cochran et al. | 250/358.1 |
| 8,512,796 B2* | 8/2013 | Felts et al. | 427/2.3 |
| 8,810,259 B2* | 8/2014 | Herrmann et al. | 324/637 |
| 2002/0018510 A1* | 2/2002 | Murphy et al. | 374/45 |
| 2005/0207468 A1* | 9/2005 | McCullough et al. | 374/5 |
| 2011/0252899 A1 | 10/2011 | Felts et al. | |
| 2012/0229147 A1 | 9/2012 | Herrmann et al. | |
| 2012/0241443 A1* | 9/2012 | Tang et al. | 219/679 |
| 2013/0291632 A1* | 11/2013 | Felts et al. | 73/150 R |

* cited by examiner

METHOD AND APPARATUS FOR IDENTIFYING DEFECTS IN SUSCEPTORS OF MICROWAVE FOOD CONTAINERS

TECHNICAL FIELD

This disclosure relates generally to microwave food containers and more specifically to microwave food containers having microwave susceptors for applying radiant and conductive heat to food in addition to microwave heating.

BACKGROUND

Microwave food containers are well known. Some such containers include microwave susceptors applied to surfaces that partially or completely surround food intended to be heated in a microwave oven. The susceptors, which may be applied in many patterns, interact with microwave energy in a microwave oven to become hot. The hot susceptors then act either as a radiant heat sources when not in direct contact with food or conductive heat sources when directly contacting food. This, in turn, can augment the internal heating of food through microwave excitation by providing surface browning or crisping mimicking that obtained in traditional radiant ovens.

Microwave susceptors of food containers often are ultra thin films of metals such as aluminum deposited by vacuum evaporation or other means upon a polyester substrate. These polyester/metal susceptors are then bonded to the paper of the container on interior surfaces thereof. The susceptors can be rapidly heated by exposure to microwaves to temperatures of 400 degrees Fahrenheit or more to provide radiant or conductive heating. Other materials have been used as susceptors including steel, copper, and Inconel® alloy. A defect such as, for instance, a cut, crack, gap, or poorly deposited area of metal in a susceptor can occur during manufacture or fabrication. Such defects only become apparent when a consumer attempts to cook a microwave dish and can manifest themselves in various ways including the production of hot spots that burn food or cold spots where heating is incomplete. Instances where containers have caught fire have been observed. Consumers obviously become agitated when this happens, and the risk of fire can be a liability for the manufacturer of microwave containers.

A need therefore exists for a method and apparatus for performing a reliable quality check on the susceptors of each microwave container during the container manufacturing process to ensure the integrity of the susceptors and thus the consistency of the cooking experience and safety for ultimate consumers. Such a method and apparatus should be able to operate reliably at throughputs equaling those of the container manufacturing line itself and should automatically reject containers that do not pass the quality check so that they do not find themselves among commercially shipped products. It is to the provision of a method and apparatus that addresses these and other needs that the present invention is primarily directed.

SUMMARY

Briefly described, a method and apparatus are disclosed that provide quality testing of the susceptors of microwave cooking containers during the manufacturing process. The quality testing is performed on every container as the containers are conveyed in a downstream direction along a processing path, and a mechanism for ejecting from the processing path containers that do not pass the quality testing is provided. The apparatus includes a set of microwave inert flight chains that carry microwave containers along the processing path for testing. A resonator cavity is disposed along the processing path and the containers pass in spaced sequence through the resonator cavity. A microwave source is coupled to the interior of the resonator cavity through a microwave horn antenna to establish a low power microwave environment within the resonator cavity. The containers are therefore exposed to low level microwave radiation as they move through the resonator cavity. This causes the susceptors of the containers to be heated, but not to temperatures high enough to destroy the susceptors for their ultimate purpose of augmenting the heating of food.

A first microwave absorbing cavity is disposed upstream of the resonator cavity and has doors that are synchronized with the flow of spaced containers to prevent leaking of microwaves from the apparatus as containers move into the resonator cavity. Similarly, a second microwave absorbing cavity is disposed downstream of the resonator cavity and also has synchronized doors to prevent leaking of microwaves as containers move out of the resonator cavity. Containers thus are moved by the flight chains along the processing path where they pass through the first microwave absorbing cavity, into and through the resonator cavity where their susceptors are exposed to microwave energy, and through the second microwave absorbing cavity. The second microwave absorbing cavity includes an infrared window and an infrared imaging device or camera arranged to capture infrared images through the infrared window of containers passing through the second microwave absorbing cavity.

As the containers move through the resonator cavity and are exposed to low level microwave radiation, the susceptors of the containers are heated through interaction with the microwave energy. The power of the microwave energy is sufficiently low that the susceptors are not permanently damaged by the heating such that the test is non-destructive. As the containers emerge from the resonator cavity, they move into and through the second microwave absorbing cavity. There, each container moves through the field-of-view of the infrared imaging device and a digital infrared image of each container is captured. The infrared image maps the temperature profiles of the susceptors applied to each container that were previously heated in the resonator cavity.

The infrared image of each container is then processed by software that determines whether each image is consistent with that expected from a container with defect-free susceptors or whether the image indicates one or more defects in the susceptors. If a defect-free determination is made, the container is considered to have passed the test and is allowed to continue along the processing path for additional processing. If a defect is indicated in a container, then the location of the container in the sequence is noted and, when the container leaves the testing station, a gate is activated to divert the defective container off of the processing path and toward a reject location. The result is that all containers of a manufacturing run are subjected to a quality test of their susceptors, which is done non-destructively, and defective containers are removed from the processing path. Accordingly, each and every container shipped to packagers and ultimately used by consumers may reliably be certified defect-free.

Thus, a method and apparatus is now disclosed that addresses the above identified needs and others and that does so in an efficient and effective manner. These and other aspects, features, and advantages of the invention disclosed herein will become more apparent to the skilled artisan upon review of the detailed description set forth below taken in

DETAILED DESCRIPTION

Figures 1, 2, 3:
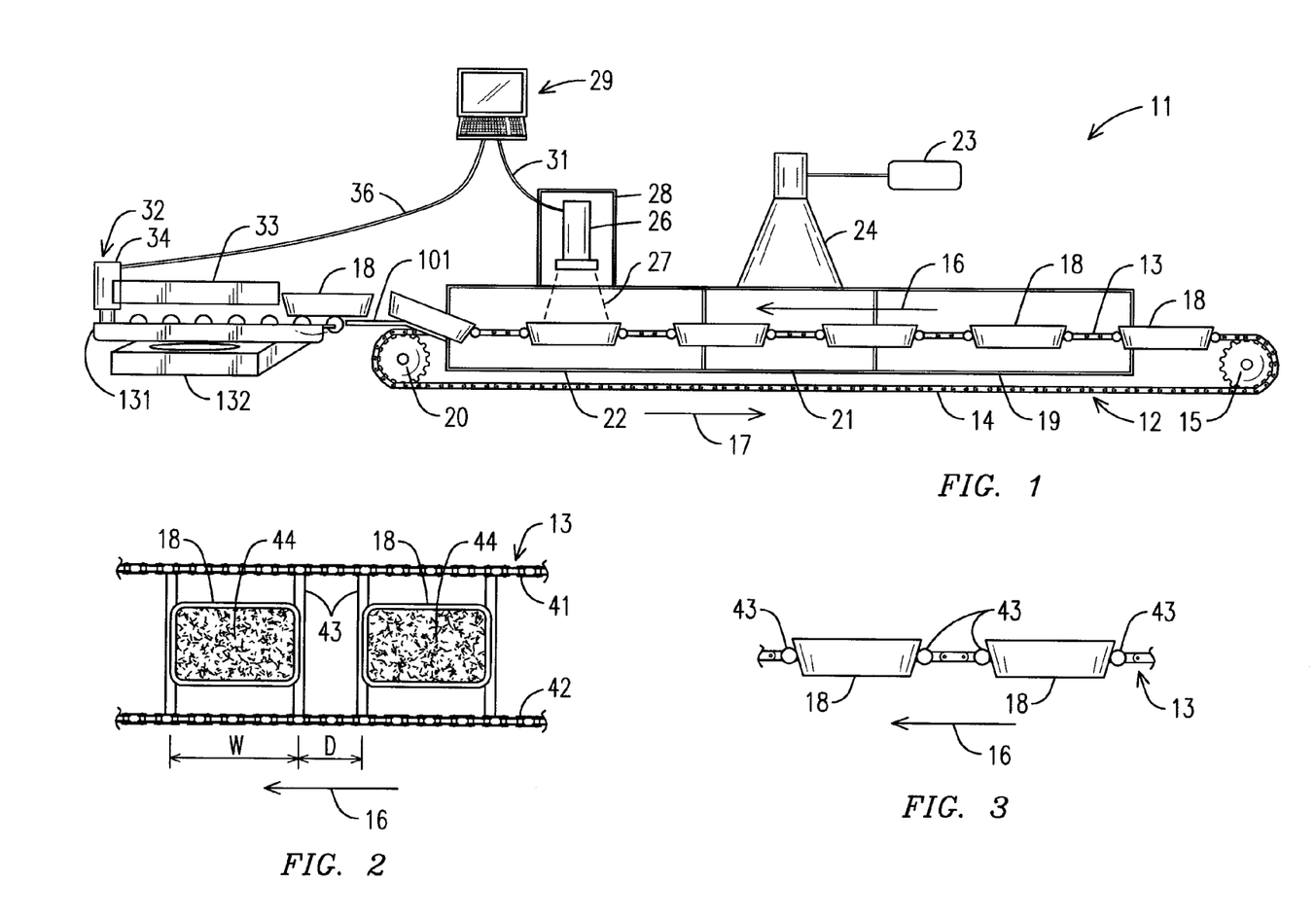
FIG. 1 is a simplified schematic view of an apparatus for identifying defects in susceptors of microwave food containers according to an embodiment of the present invention.
FIG. 2 is a top view of microwave food trays being carried by a microwave inert flight chain for testing according to the invention.
FIG. 3 is a side view of the microwave food trays of FIG. 2 illustrating support of each tray between microwave inert rods extending between the flight chains.

Reference will now be made in more detail to the drawing figures, wherein like reference numbers indicate like parts throughout the several views. FIG. 1 is a schematic view of an apparatus 11 that embodies principles of the invention. The apparatus 11 comprises an endless chain conveyor 12 having an upper flight 13 and a lower flight 14. The chains 41 and 42 (FIG. 2) of the conveyor 12 are supported by sprockets 15 and 20 and at least one of the sprockets is driven to move the chains of the conveyor. The links of the chains are made of a non-metallic or otherwise microwave inert material such as a polymer. The upper flight of the conveyor moves in a downstream direction along a processing path as indicated by arrow 16 and the lower or return flight moves in the upstream direction as indicated by arrow 17. Referring briefly to FIG. 2, spaced pairs of support rods 43 extend between the chains 41 and 42 of the conveyor and each pair of support rods 43 is spaced a distance W apart to support a microwave food container 18 nestled between the support bars. Each pair of support bars is spaced from adjacent pairs of support bars a distance D.

Referring again to FIG. 1, microwave food containers 18 are moved by the endless chain conveyor 12 through three adjacent stations comprising an upstream microwave absorbing chamber 19, a microwave resonator chamber 21, and a downstream microwave absorbing chamber 22. The microwave food containers 18 have microwave susceptors 44 (FIG. 2) on one or more of their surfaces, which are heated when exposed to microwave energy to assist in the cooking, browning, or crisping of food contained within the containers. A solid state microwave generator 23 generates microwaves that are coupled to the resonator chamber 21 through a linearly polarized microwave horn antenna 24. In this way, the microwave food containers 18 are subjected or exposed to microwave radiation as they traverse the microwave resonator cavity. The upstream microwave absorbing chamber 19 and the downstream microwave absorbing cavity are configured, as detailed below, to prevent microwave energy from the resonator chamber 21 from leaking to the atmosphere, where it can be harmful to workers.

In addition to preventing leakage of microwave energy, the downstream microwave absorbing chamber 22 includes an infrared (IR) imaging device 26 having a field-of-view 27 that encompasses microwave food containers 18 as the containers move through the downstream microwave absorbing chamber 22. The infrared imaging device 26 views containers through an IR window 98 (FIG. 9) in the downstream microwave absorbing cavity and is enclosed in a Faraday cage 28 to prevent leakage of microwave energy through the IR window. The infrared imaging device 26 produces digital images that are conveyed via cable 31 to a computer controller 29, which receives digital infrared images of food containers for processing. The computer controller 29 may be a programmable logic controller (PLC) or any programmable controller suitable to the task.

As microwave food containers 18 move out of the downstream microwave absorbing cavity, they are lifted off of the conveyor 12 by a recovery plate 101. From the recovery plate, the microwave food containers move to a roller-type sorting station 32 comprising a main conveyor 131 and a discard conveyor 132. The sorting station 32 includes a mechanical swing arm 33 that can be swung by a servo motor 34 between a first position allowing microwave food containers to continue downstream on the main conveyor 131 and a second position engaging and diverting microwave food containers onto the discard conveyor 132. The servo motor 34 is connected by cable 36 to the computer controller 29, which can activate the servo motor 34 to move the mechanical swing arm 33 from its first position to its second position and vice versa.

Generally speaking, operation of the apparatus 11 is as follows. Microwave food containers 18 are moved by the endless chain conveyor 12 through the upstream microwave absorbing cavity. As discussed in more detail below, the upstream microwave absorbing cavity has an entry door and an exit door and the spacing between the doors is coordinated with the spacing between the containers such that at least one of the doors is closed at all times to prevent microwave energy leakage. From the upstream microwave absorbing chamber 19, the microwave food containers 18 move through the microwave resonator chamber 21, where they are exposed to low level microwave energy from the microwave generator 23. The level of microwave energy is sufficient to heat the susceptors 44 of each container 18 but low enough not to destroy the susceptors. It has been found that microwave energy of less than about 20 watts is sufficient for this purpose, although any level might be chosen depending upon container configuration, size, and susceptor layout. It is thus believed that a solid state microwave generator with a maximum output of about 100 watts will be sufficient.

Each microwave food container 18 moves out of the microwave resonator chamber 21 and into the downstream microwave absorbing chamber 22 with its susceptors having been heated by microwave energy in the resonator cavity. As each container 18 moves into the field-of-view 27 of the infrared imaging device 26, a digital infrared image is obtained of the container and uploaded to the computer controller 29. There, the image is analyzed by software and a determination is made whether the infrared image indicates that the corresponding microwave food container has any defective susceptors. More specifically, defects such as cuts, cracks, or gaps in the conductive material of a susceptor will cause a discontinuity in current flow at the defect. This, in turn, causes the susceptor to exhibit an elevated temperature or "hot spot" at the locations of any defects when exposed to microwave energy in the resonator chamber. The hot spot will register as an elevated temperature in the infrared image obtained by the infrared imaging device 26. The computer controller 29 is programmed to detect images exhibiting such an elevated temperature (or any other feature or features of the images indicative of susceptor defects) and to assign a "fail" status to containers showing indications of susceptor defects. Containers that do not exhibit elevated temperatures are assigned a "pass" status by the software of the computer controller 29.

Each microwave food container 18 next moves out of the downstream microwave absorbing chamber 22, is removed from the conveyor 12 by recovery plate 101, and moves to the sorting station with the main conveyor 131 and the discard conveyor 132. If a container has been assigned a "pass" status, the computer controller 29 signals the servo motor 34 to maintain the mechanical swing arm 33 in its first position allowing the container to continue downstream for further processing to be shipped to customers. However, if a container has been assigned a "fail" condition, the computer controller signals the servo motor 34 to move the mechanical swing arm 33 to its second position. When the defective container engages the mechanical swing arm 33, it is diverted thereby from the main conveyor 131 onto the discard conveyor 132, which carries it to a remote location for discard, study, or other purposes. Thus, all microwave food containers 18 showing indications of defects in their susceptors are removed from the stream of containers exhibiting no such defects. It may thus be certified that all containers that are shipped to customers are tested and that their susceptors are defect free.

FIGS. 2 and 3 illustrate one possible embodiment of the endless chain conveyor 12 from the top (FIG. 2) and from the side (FIG. 3). The endless chain conveyor 12 (only the upper flight 13 is illustrated in these figures) comprises two spaced apart microwave inert chains 41 and 42 with spaced pairs of support rods 43 extending therebetween. The distance between the support rods 43 is such that a microwave food container 18 with susceptors 44 can be supported between the support bars for movement in the downstream direction 16. More specifically, the distance W between the two support rods 43 of each pair is between the length of the bottom of a container 18 and the length of the top of a container. In this way, containers nestle between the support bars and are supported thereby but nevertheless can be lifted easily off of the conveyor 13. The distance between each pair of support bars is D, where D preferably is equal to W/2 for reasons explained below.

Figure 4:
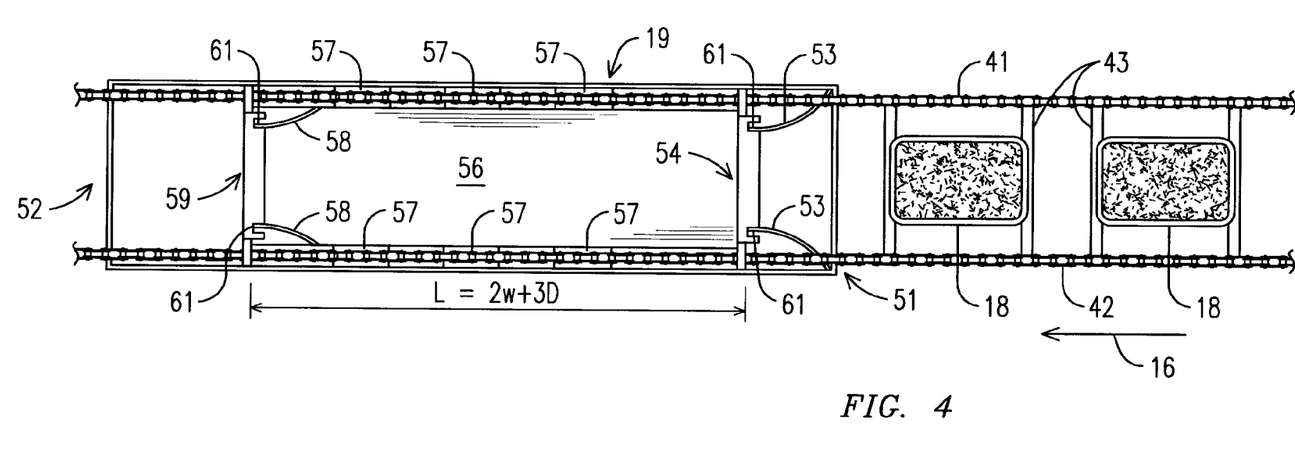
FIG. 4 is a top schematic view illustrating microwave food trays being moved into the first microwave absorbing cavity.
Figure 5:
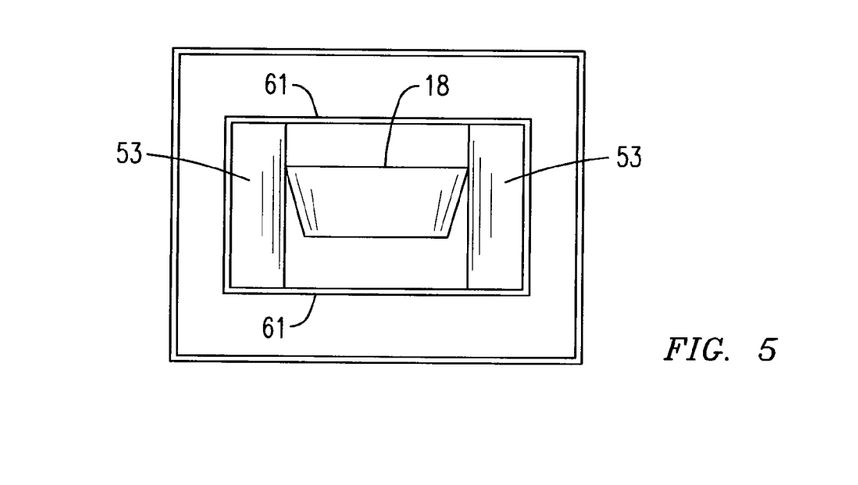
FIG. 5 is a schematic view from the downstream direction showing microwave food containers moving into the first microwave absorbing cavity and being centered by the centering guide of the cavity.
Figure 6:
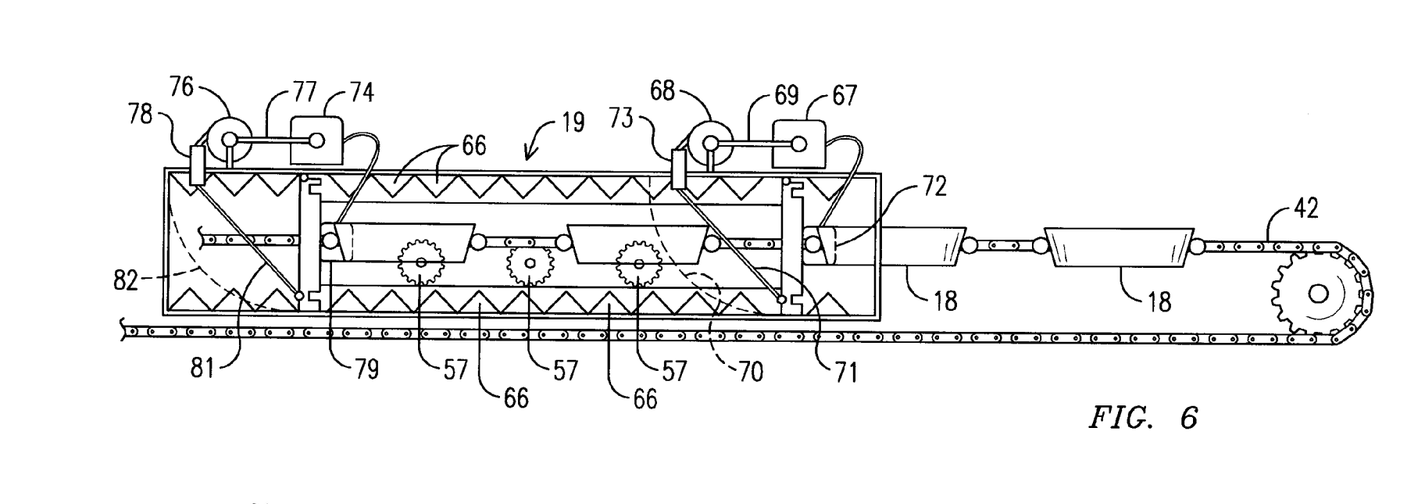
FIG. 6 is a side schematic view of the first microwave absorbing cavity illustrating synchronized operation of the doors of the cavity to prevent leakage of microwave energy from the system.

FIGS. 4-6 illustrate in more detail the upstream microwave absorbing chamber 19 and its function. The upstream microwave absorbing chamber 19 has a box-like body that defines the inner cavity 56. The upper flight 13 of the endless chain conveyor moves through the inner cavity 56 in downstream direction 16 to carry microwave food containers 18 sequentially along a processing path through the cavity 56. An entry door 54 is disposed at the upstream end of the cavity 56 and an exit door 59 is disposed at the downstream end of the cavity. As shown in FIG. 6, the interior walls of the cavity body is lined with honeycomb microwave absorbing material 66, which functions to absorb or otherwise dissipate microwave energy that may enter the cavity 54. A first pair of centering guides 53 is disposed just upstream of the entry door 54 and a second pair of centering guides 58 is disposed just upstream of the exit door 59. As perhaps best shown in FIG. 5, the centering guides urge the microwave food containers to the center of the microwave absorbing cavity 56 just before the containers enter and just before they leave the cavity 56.

Referring to FIG. 6, each of the doors of the microwave absorbing chamber 19 is hinged at the top so that it is opened by swinging up and closed by swinging down as indicated by dashed arcs 70 and 82. Each door is provided around its edges with a microwave choke 61 having a thickness equal to one-quarter of the wavelength of microwave energy used in the system. This ensures that there is no leakage of microwave energy around the edges of the doors when they are closed. The default position of the doors is the closed position, where the doors are held firmly flat on the edges of the cavity opening by a spring (not shown). A metal string 71, 81 is attached to the lower portion of each of the doors and each metal string 71, 81 passes through a microwave string choke 73, 78 out of the cavity 56. Each of the metal strings 71, 81 winds about a corresponding roller-type pulley 68, 76 that can be driven by a servo motor 67, 74 to wind up the string to open the corresponding door or to pay out the string to close the corresponding door.

A laser actuator 72, 79 is disposed just upstream of each door 54, 59 and includes a laser that projects a beam of laser light across the path of microwave food containers to a receiver on the opposite side of the path. When a container moves between the laser and its receiver, the light is blocked and this signals the servo motor 67, 74 to retract the corresponding door 54, 59 to its open position allowing the container to pass. When the container moves past the beam of laser light, projection onto the receiver is restored and this signals the servo motor to lower the door back to its closed position. Thus, the doors 54 and 59 automatically open upon the approach of a microwave food container and automatically close after the container moves into the microwave absorbing cavity 56.

The trajectories of the swinging doors are along the direction of tray movement to prevent the doors from jamming. The distance between the entry door 54 and the exit door 59 is equal to 2W+3D. This establishes a time interval between opening and closing of the two doors that is equivalent to the time required for a microwave food container to traverse D length. Thus, the entry door opens to allow entrance of one incoming food container and during this time the exit door is closed. The entry door closes just before the exit door opens to allow exit of a microwave food container from the microwave absorbing cavity and into the microwave resonator chamber 21. It will thus be seen that the described geometry allows for one of the two doors to be closed at all times to block leakage of microwave energy from the microwave resonator cavity. It is anticipated that any small amounts of microwave energy that may leak past the exit door 59 (since it is directly adjacent the microwave resonator cavity) will be dissipated on the honeycomb microwave absorbing walls 66 of the cavity 56 and thus will not leak from the entry door 54 when the entry door is open.

Figure 7:
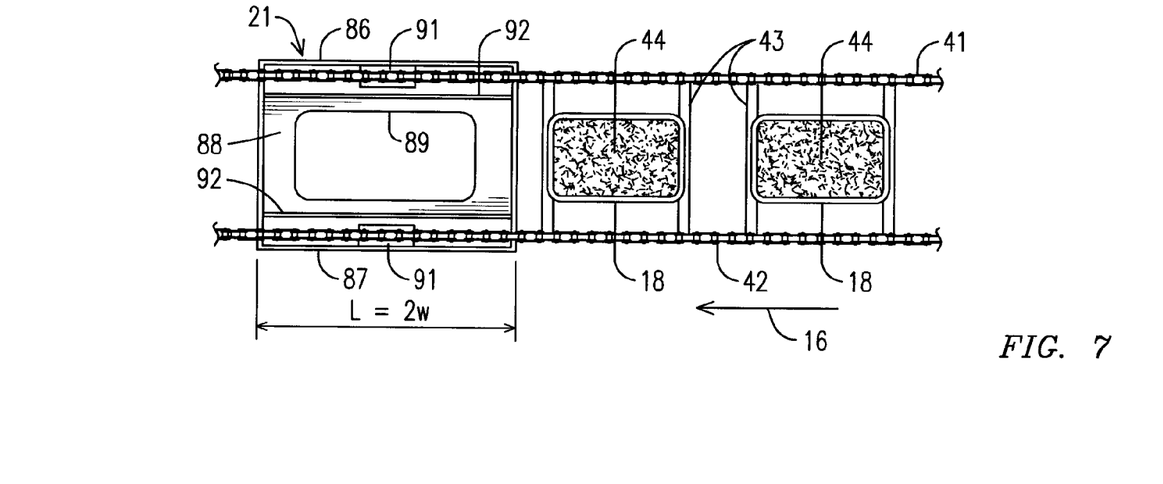
FIG. 7 is a top schematic view illustrating microwave food trays being moved from the first microwave absorbing cavity into the resonator cavity according to an embodiment of the invention.
Figure 8:
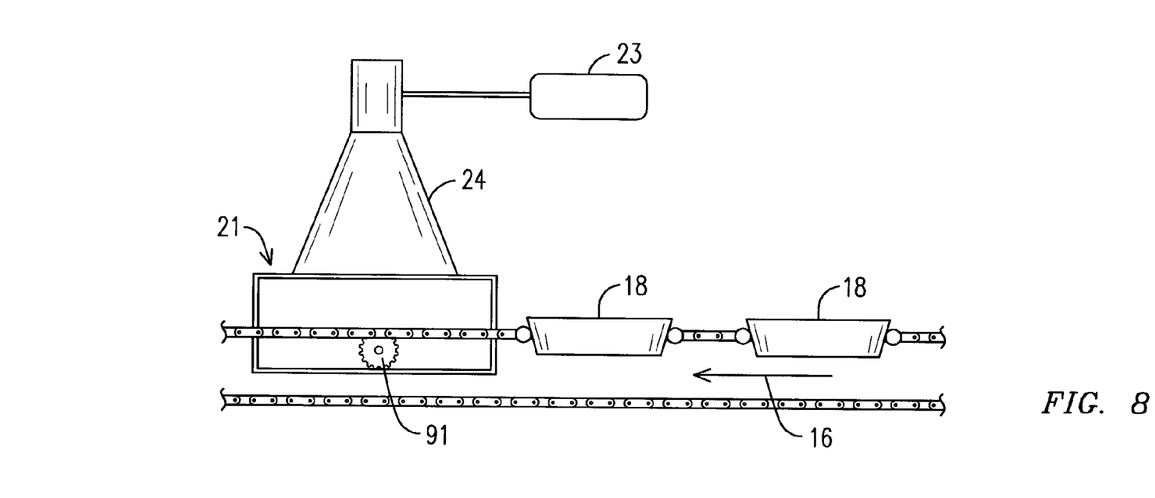
FIG. 8 is a side schematic view of the resonator cavity illustrating the microwave horn antenna and microwave generator for producing microwaves within the resonator cavity.

FIGS. 7 and 8 illustrate in schematic form the microwave resonator chamber 21 and the movement of microwave food containers 18 therethrough. The chamber 21 is generally rectangular with exterior walls that enclose the resonator cavity therein. A pair of laterally adjustable metal plate side walls 92 is disposed within the cavity and side walls can be adjusted toward and away from each other to adjust the width of the waveguide defined in the cavity. In this way, the microwave field distribution within the cavity can be adjusted and controlled to ensure equal microwave treatment on the surfaces of microwave food containers and microwave susceptors thereon.

An antenna window 89 is formed in the top wall of the resonator chamber 21 and a linearly polarized horn antenna applicator 24 mounts to the resonator chamber around the window 89. The horn antenna is fed by a solid state microwave generator 23 at a specific wavelength and power and the resulting microwave radiation is applied to the resonator cavity within the resonator chamber 21 through the horn antenna applicator. A microwave field is thus established in the resonator cavity and this field induces electric currents within the microwave susceptors of the food containers moving through the resonator cavity. The induced electric currents heat the susceptors due to their inherent electrical resistance. The relatively low power of the microwave radiation heats the susceptors sufficiently to reveal any defects as discussed above but does not generate enough heat to destroy the susceptors for ultimate use by consumers to heat foods packaged in the containers.

Figure 9:
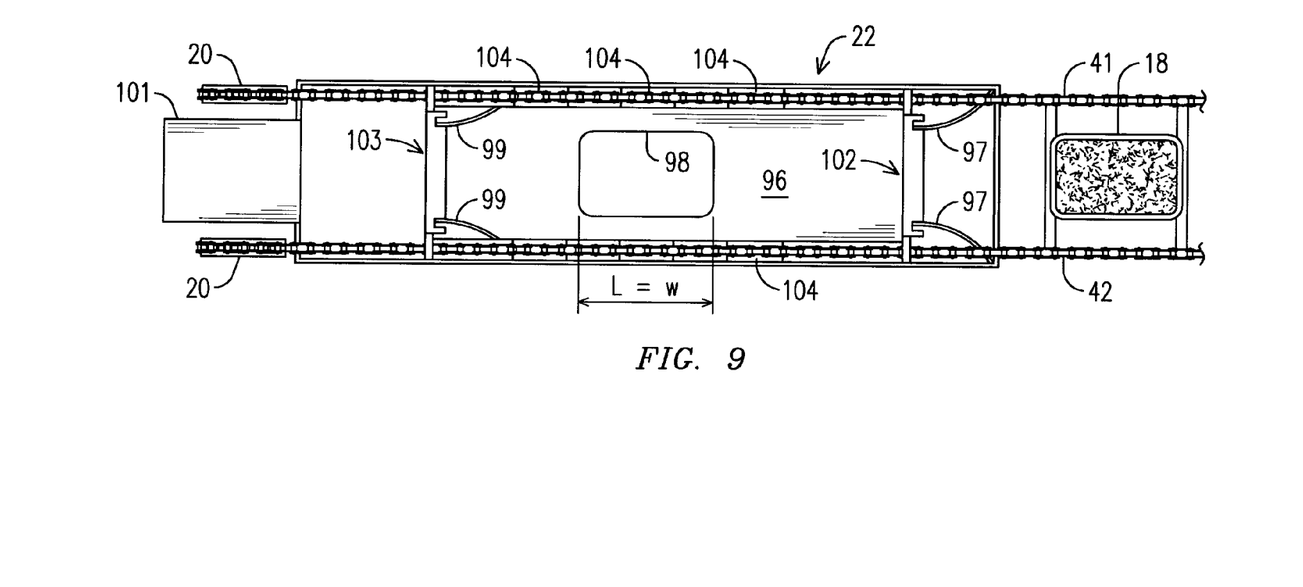
FIG. 9 is a top schematic view of the second microwave absorbing cavity illustrating one possible placement of an infrared window into the cavity.
Figure 10:
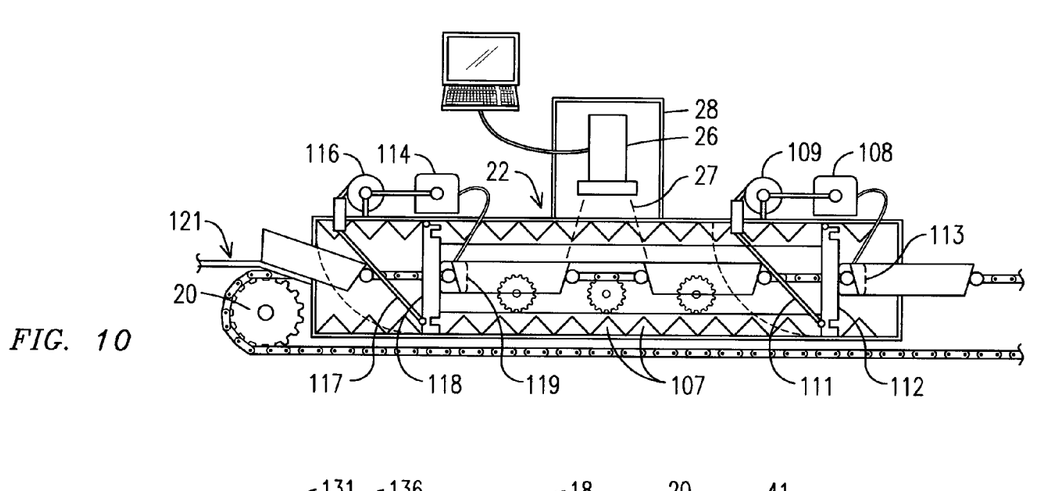
FIG. 10 is a side schematic view of the second microwave absorbing cavity showing the microwave camera and Faraday shield enclosing the camera to prevent leakage of microwave energy.

FIGS. 9 and 10 illustrate in schematic form the downstream microwave absorbing chamber 22. With regard to its function of preventing leakage of microwave energy into the environment, the downstream microwave absorbing chamber 22 functions in the same manner as the upstream microwave absorbing chamber 19, which is described in detail above. So, a discussion of the features of the downstream microwave absorbing chamber 22 that achieve this function need not be repeated here. However, the downstream chamber carries additional features that permit the acquisition of infrared images of infrared food containers passing through the downstream microwave absorbing chamber 22, and these features will be described in more detail.

As shown in FIG. 9, the top wall of the downstream microwave absorbing chamber 22 is provided with an IR window 98 into the cavity defined within the chamber. The IR window 98 preferably is made of a material that transmits infrared radiation and an infrared imaging device such as an IR camera 26 is arranged to peer through the IR window into the cavity below. The IR imaging device 26 preferably has a field-of-view 27 that encompasses microwave food containers moving through the microwave absorbing cavity, or at least any areas on the containers that have microwave susceptors applied thereto. Since microwave energy has a long wavelength that is likely also to pass through the IR window, the infrared imaging device is enclosed in a Faraday cage 28 constructed to prevent passage of microwave energy of the wavelength being used in the system. In this way, the function of the downstream microwave absorbing chamber to prevent microwave leakage is maintained. The infrared imaging device 26 is connected to the computer controller and transmits digital infrared images of each microwave food container to the computer controller.

The IR image of each container essentially shows a temperature map of the microwave susceptors applied to surfaces of the container, which have been heated by exposure to microwave energy in the resonator chamber 21. As mentioned above, defects such as cuts, cracks, or gaps in the conductive material of a susceptor will cause a discontinuity in electric current flow at the defect. This, in turn, causes the susceptor to exhibit an elevated temperature or "hot spot" at the locations of any defects when exposed to microwave energy in the resonator chamber. The hot spot will register as an elevated temperature in the infrared image obtained by the infrared imaging device 26. The computer controller 29 is programmed to detect images exhibiting such an elevated temperature (or any other features of the images indicative of susceptor defects) and to assign a "fail" status to containers showing indications of susceptor defects. Containers that do not exhibit elevated temperatures are assigned a "pass" status by the software program of the computer controller.

Figure 11:
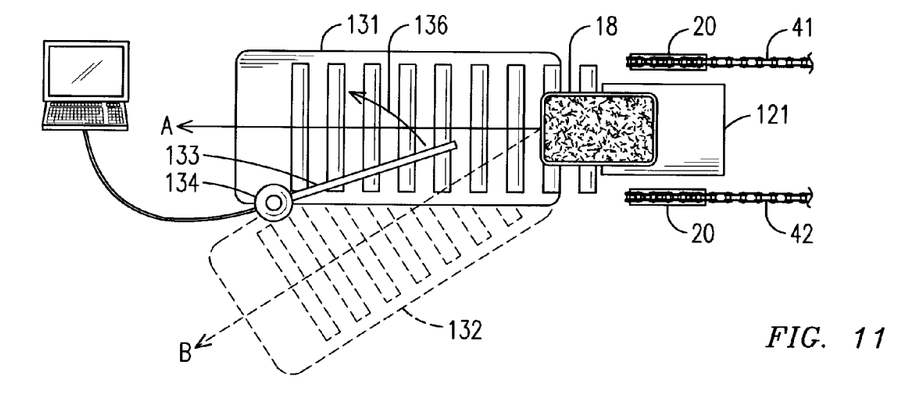
FIG. 11 is a top schematic view illustrating microwave containers exiting the second microwave absorbing cavity onto a conveyor system where containers identified as being defective are diverted to a reject conveyor and containers identified as being defect free move on along the processing line.

As each microwave food container, now tested for susceptor defects, exits the downstream microwave absorption chamber 22, it is pushed up a ramp onto a recovery plate 121, thus removing it from the endless chain conveyor 12. As shown in FIG. 11, each container then moves from the recovery tray 121 onto the main conveyor 131 of the sorting station 32 for sorting defective containers from good containers. The sorting station 32 includes a mechanical swing arm 133 that can be moved by a servo motor from a first position extending along a side of the main conveyor to a second position extending across the main conveyor at an angle. This movement is indicated by arrow 136 in FIG. 11. When the swing arm is in its first position, microwave food containers continue to move past the mechanical swing arm in the downstream direction A to be prepared for shipment to customers. When the swing arm is in its second position, it engages the next approaching microwave food container and diverts it sideways onto a reject conveyor 132, which conveys the container in direction B to a remote location to be discarded, studied, or otherwise disposed of.

The computer controller is operatively connected to the servo motor of the mechanical swing arm and keeps track of the sequence of containers moving along in the downstream direction. The computer controller previously determined for each container, as described above, whether the container was assigned a "pass" or a "fail" status based upon the infrared image obtained from the container. Thus, as a container with a "pass" status approaches the sorting station, the mechanical swing arm is placed in its first position allowing the passing container to continue on in direction A. When a container that was assigned a "fail" status approaches the sorting station, the computer controller places the mechanical swing arm in its second position thereby diverting the defective container in direction B so that it does not end up among the containers sent to customers.

It will thus be seen that each microwave food container is tested for defects in its microwave susceptors prior to being shipped to customers for use. Defective containers, which can result in uneven or unpredictable heating of food or even fire in some cases, are removed and only containers without susceptor defects are delivered. Further, the non-destructive testing of each container can be accomplished at normal line speeds of the container fabrication line by appropriately setting the microwave power, resonator cavity size, and image acquisition timing.

The invention has been described herein in terms of preferred embodiments and methodologies considered by the inventors to represent the best mode of carrying out the invention. However, the preferred embodiments should not be construed to be limiting but only as examples of possible ways of carrying out the invention itself. For example, any structure for preventing microwave leakage from the resonator chamber may be substituted for the disclosed microwave absorbing chambers. Microwaves may be applied to the resonator cavity through other than the disclosed horn antenna applicator. While images in the infrared spectrum are considered to be preferable, the invention is not limited to obtaining and analyzing infrared images and images at other wavelengths may be used if desired. It will be understood by the skilled artisan that these and a wide range of other additions, deletions, and modifications, both subtle and gross, may be made to the illustrated and exemplary embodiments without departing from the spirit and scope of the invention, which is set forth and delimited only by the claims.

What is claimed is:

1. A method of detecting defects in susceptors of microwave food containers comprising the steps of:
    (a) advancing the microwave food containers in a downstream direction along a processing path;
    (b) subjecting each microwave food container as it moves along the processing path to microwave radiation sufficient to heat the susceptors of the container without destroying the susceptors of the container;
    (c) obtaining an image of the heated susceptors of each container;
    (d) determining for each container if the image is indicative of a defect in the susceptors of the container; and
    (e) separating containers that are indicated to have a defect in their susceptors from containers that are indicated not to have a defect in their susceptors.

2. The method of claim 1 wherein step (a) comprises supporting the microwave food containers between flight chains and moving the flight chains in the downstream direction.

3. The method of claim 2 wherein the flight chains are fabricated of microwave inert material.

4. The method of claim 2 and wherein the step of supporting the microwave food containers comprises disposing rods in spaced relationship between the flight chains and resting the microwave food containers on the rods.

5. The method of claim 1 wherein step (b) comprises moving the microwave food containers through a resonator cavity disposed along the processing path and applying microwave energy to the resonator cavity.

6. The method of claim 5 wherein the step of applying microwave energy comprises generating microwave energy with a microwave generator and coupling the generated microwave energy to the resonator cavity.

7. The method of claim 6 wherein the step of coupling the generated microwave energy to the resonator cavity comprises directing the microwave energy through a horn antenna applicator coupled to the resonator cavity.

8. The method of claim 1 wherein step (c) comprises moving each microwave food container through the field-of-view of an imaging device and activating the imaging device to produce an image of the microwave food container.

9. The method of claim 1 wherein step (d) comprises comparing the image of step (c) to a predetermined criteria, determining the differences between the image and the predetermined criteria, and determining that the image is indicative of a defect if the differences between the image and the predetermined criteria exceed predetermined thresholds.

10. The method of claim 1 wherein step (e) comprises diverting containers that are indicated to have a defect in their susceptors away from the processing path.

11. The method of claim 1 further comprising advancing the microwave food containers through a first microwave absorbing cavity prior to step (b).

12. The method of claim 1 further comprising advancing the microwave food containers through a second microwave absorbing cavity after step (b).

13. The method of claim 12 wherein step (c) is performed while the microwave food containers are in the second microwave absorbing cavity.

14. The method of claim 1 wherein step (c) comprises obtaining an infrared image.

15. An apparatus for detecting defects in susceptors of microwave food containers comprising:
    a conveyor configured to advance the microwave food containers in a downstream direction along a processing path;
    a microwave resonator cavity disposed along the processing path and configured such that the microwave food containers move through the microwave resonator cavity as they advance along the processing path;
    a microwave generator;
    an applicator coupling the microwave generator to the microwave resonator to establish a microwave energy field within the microwave resonator;
    the microwave energy field being sufficient to heat susceptors of the microwave food containers without destroying the susceptors;
    an imaging device for capturing an image of the heated susceptors of each microwave food container;
    a computer controller programmed to determine if the image of each microwave food container is indicative of a defect in the susceptors of the container; and
    a mechanism controlled by the computer controller for separating microwave food containers with defective susceptors from microwave food containers without defective susceptors.

16. An apparatus according to claim 15 further comprising a first microwave absorbing cavity disposed along the processing path upstream of the resonator cavity and configured such that microwave food containers move through the first microwave absorbing cavity before moving through the resonator cavity, the microwave absorbing cavity preventing leakage of microwave energy from the microwave resonator into the environment.

17. An apparatus according to claim 16 wherein the first microwave absorbing cavity has an entrance end and an exit end and further comprising an entry door at the entrance end of the microwave absorbing cavity and an exit door at the exit end of the microwave absorbing cavity, the doors being controlled such that at least one of the doors is closed at all times as the microwave food containers move through the first microwave absorbing cavity.

18. An apparatus according to claim 17 further comprising a second microwave absorbing cavity disposed along the processing path downstream of the resonator cavity and configured such that microwave food containers move through the second microwave absorbing cavity after moving through the resonator cavity, the second microwave absorbing cavity preventing leakage of microwave energy from the microwave resonator into the environment.

19. An apparatus according to claim 18 wherein the second microwave absorbing cavity has an entrance end and an exit end and further comprising an entry door at the entrance end of the second microwave absorbing cavity and an exit door at the exit end of the second microwave absorbing cavity, the doors being controlled such that at least one of the doors is closed at all times as the microwave food containers move through the second microwave absorbing cavity.

20. An apparatus according to claim 19 further comprising a window formed in the second microwave absorbing cavity, the imaging device imaging microwave food containers through the window as the containers move through the second microwave absorbing cavity.

21. An apparatus according to claim 20 further comprising a Faraday cage enclosing the image device to prevent leakage of microwave energy through the window.

22. A method of detecting defects in susceptors of microwave food containers as the containers are conveyed along a processing path in a downstream direction, the method comprising the steps of heating the susceptors of each microwave food container, obtaining an image of the heated susceptors, and determining based upon the image whether defects in the susceptors are indicated.

23. The method of claim 22 wherein the step of heating the susceptors comprises exposing each microwave food container to microwave energy sufficient to heat the susceptors while not destroying the susceptors for their intended final use.

24. The method of claim 23 wherein the step of obtaining an image of the heated susceptors comprises obtaining an infrared image of the heated susceptors.

25. The method of claim 24 wherein the step of determining whether defects in the susceptors are indicated comprises comparing the infrared image of each microwave food container to predetermined criteria and determining that defects are indicated if the infrared image deviates from the predetermined criteria by a predetermined amount.

26. The method of claim 25 further comprising preventing microwave energy from escaping into the atmosphere as microwave food containers are exposed to the microwave energy.

27. The method of claim 25 wherein the predetermined criteria is a maximum temperature.

\* \* \* \* \*